(12) United States Patent
Wong

(10) Patent No.: US 10,518,077 B2
(45) Date of Patent: *Dec. 31, 2019

(54) MECHANICAL FRICTION ENHANCEMENT FOR THREADED CONNECTION INCORPORATING CRUSHABLE RIBS

(71) Applicant: Becton Dickinson and Company Limited, Dun Laoghaire (IE)

(72) Inventor: Andrew Wong, East Hanover, NJ (US)

(73) Assignee: Becton Dickinson and Company Limited, Dun Laoghaire (IE)

(*) Notice: Subject to any disclaimer, the term of this patent is extended or adjusted under 35 U.S.C. 154(b) by 10 days.

This patent is subject to a terminal disclaimer.

(21) Appl. No.: 15/837,399

(22) Filed: Dec. 11, 2017

(65) Prior Publication Data

US 2018/0098916 A1    Apr. 12, 2018

Related U.S. Application Data

(63) Continuation of application No. 14/278,684, filed on May 15, 2014, now Pat. No. 9,968,771.

(60) Provisional application No. 61/824,179, filed on May 16, 2013.

(51) Int. Cl.
    *A61M 39/10*    (2006.01)
    *A61J 1/20*    (2006.01)

(52) U.S. Cl.
    CPC ........ *A61M 39/1011* (2013.01); *A61J 1/2096* (2013.01); *A61M 2039/1033* (2013.01); *A61M 2039/1044* (2013.01); *Y10T 29/49948* (2015.01)

(58) Field of Classification Search
    CPC .................................................. A61M 39/1011
    See application file for complete search history.

(56) References Cited

U.S. PATENT DOCUMENTS

| 2,612,285 A | 9/1952 | Benson |
| 3,405,831 A | 10/1968 | Hudson |
| 3,435,978 A | 4/1969 | Wittwer |
| 3,682,345 A | 8/1972 | Baugh |
| 3,741,421 A | 6/1973 | Wittwer |
| 3,876,234 A | 4/1975 | Harms |
| 4,360,024 A | 11/1982 | Wallace |
| 4,452,473 A | 6/1984 | Ruschke |
| 4,629,455 A | 12/1986 | Kanno |
| 4,735,441 A | 4/1988 | Stephens |
| 5,112,318 A | 5/1992 | Novacek et al. |
| 5,176,415 A | 1/1993 | Choksi |

(Continued)

FOREIGN PATENT DOCUMENTS

| EP | 0158030 A1 | 10/1985 |
| GB | 2353078 A | 2/2001 |

(Continued)

*Primary Examiner* — Nathan R Price
*Assistant Examiner* — Melissa A Snyder
(74) *Attorney, Agent, or Firm* — The Webb Law Firm

(57) ABSTRACT

A medical connector includes a body having a distal end, a proximal end, and a sidewall extending between the distal end and the proximal end, a helical thread extending radially outward from a surface of the sidewall and comprising a crest portion, flank portions, and a root portion with the flank portions connecting the crest portion to the root portion, and at least one deformable protrusion extending radially outward from the root portion of the helical thread.

18 Claims, 11 Drawing Sheets

(56) References Cited

U.S. PATENT DOCUMENTS

| | | |
|---|---|---|
| 5,213,225 A | 5/1993 | King et al. |
| 5,263,945 A | 11/1993 | Byrnes et al. |
| 5,312,377 A | 5/1994 | Dalton |
| 5,591,143 A | 1/1997 | Trombley, III et al. |
| 5,620,427 A | 4/1997 | Werschmidt et al. |
| 5,651,776 A | 7/1997 | Appling et al. |
| 5,702,374 A | 12/1997 | Johnson |
| 5,845,798 A * | 12/1998 | Carrier ............ B65D 41/0471 215/330 |
| 5,855,568 A * | 1/1999 | Battiato ............ A61M 5/14546 604/240 |
| 5,871,473 A | 2/1999 | Strauss et al. |
| 5,984,373 A | 11/1999 | Fitoussi et al. |
| 6,074,373 A | 6/2000 | Sudo et al. |
| 6,152,913 A | 11/2000 | Feith et al. |
| 6,224,588 B1 * | 5/2001 | Jentzen ............... A61M 5/347 604/241 |
| 6,645,178 B1 | 11/2003 | Junker et al. |
| 6,673,059 B2 | 1/2004 | Guala |
| 6,722,705 B2 | 4/2004 | Korkor |
| 6,843,513 B2 | 1/2005 | Guala |
| 6,869,426 B2 | 3/2005 | Ganem |
| 6,893,056 B2 | 5/2005 | Guala |
| 7,128,348 B2 | 10/2006 | Kawamura et al. |
| 7,314,061 B2 | 1/2008 | Peppel |
| 7,347,458 B2 | 3/2008 | Rome et al. |
| 7,503,596 B2 | 3/2009 | Rome et al. |
| 7,523,967 B2 | 4/2009 | Steppe |
| 7,618,072 B2 | 11/2009 | Funamura et al. |
| 7,708,714 B2 | 5/2010 | Connell et al. |
| 7,722,090 B2 | 5/2010 | Burton et al. |
| 7,740,288 B2 | 6/2010 | Mantell |
| 7,998,133 B2 | 8/2011 | Fago et al. |
| 7,998,134 B2 | 8/2011 | Fangrow et al. |
| 8,038,182 B2 | 10/2011 | Kurimoto et al. |
| 8,162,897 B2 | 4/2012 | Byrum |
| 8,262,644 B2 | 9/2012 | Fago et al. |
| 8,286,936 B2 | 10/2012 | Kitani et al. |
| 8,287,518 B2 | 10/2012 | Kitani et al. |
| 8,372,057 B2 | 2/2013 | Cude et al. |
| 8,372,059 B2 | 2/2013 | Ziman |
| 9,114,242 B2 | 8/2015 | Fangrow et al. |
| 2003/0073959 A1 | 4/2003 | Koska |
| 2004/0238776 A1 | 12/2004 | Peters et al. |
| 2006/0089603 A1 | 4/2006 | Truitt et al. |
| 2008/0004600 A1 | 1/2008 | Kitani et al. |
| 2008/0103485 A1 | 5/2008 | Kruger |
| 2008/0140020 A1 | 6/2008 | Shirley |
| 2008/0140055 A1 | 6/2008 | Shirley |
| 2008/0287919 A1 | 11/2008 | Kimball |
| 2009/0143746 A1 | 6/2009 | Mudd et al. |
| 2009/0163859 A1 | 6/2009 | Lloyd et al. |
| 2009/0177186 A1 | 7/2009 | Delano |
| 2009/0187166 A1 | 7/2009 | Young |
| 2010/0022951 A1 | 1/2010 | Ferrera et al. |
| 2010/0036365 A1 | 2/2010 | Becker |
| 2010/0089475 A1 | 4/2010 | Tracey |
| 2010/0152669 A1 | 6/2010 | Rosenquist |
| 2010/0283238 A1 | 11/2010 | Deighan et al. |
| 2011/0095528 A1 | 4/2011 | Forberg |
| 2011/0165020 A1 | 7/2011 | Tryggvason et al. |
| 2012/0041425 A1 | 2/2012 | Tsunematsu et al. |
| 2012/0116355 A1 | 5/2012 | Heinz et al. |
| 2012/0209252 A1 | 8/2012 | Nikitina et al. |
| 2012/0305516 A1 | 12/2012 | Kuzma et al. |
| 2013/0046255 A1 | 2/2013 | Ziman et al. |
| 2013/0069365 A1 | 3/2013 | Pokorney |
| 2013/0076030 A1 | 3/2013 | Fog et al. |
| 2013/0079754 A1 | 3/2013 | Sheffer |
| 2013/0103003 A1 | 4/2013 | Capitaine et al. |
| 2014/0265319 A1 * | 9/2014 | Clark ............... A61M 39/1011 285/330 |

FOREIGN PATENT DOCUMENTS

| | | |
|---|---|---|
| JP | 5506416 B2 | 9/1993 |
| JP | 200372793 A | 3/2003 |
| JP | 2005466 A | 1/2005 |
| WO | 2008144447 A2 | 11/2008 |

* cited by examiner

MECHANICAL FRICTION ENHANCEMENT FOR THREADED CONNECTION INCORPORATING CRUSHABLE RIBS

CROSS-REFERENCE TO RELATED APPLICATION

This application is a continuation of U.S. patent application Ser. No. 14/278,684, filed May 15, 2014, which claims priority to U.S. Provisional Application Ser. No. 61/824,179, filed May 16, 2013, each of which are hereby incorporated by reference in their entirety.

BACKGROUND OF THE INVENTION

Field of the Invention

The present invention relates to a connector for enabling fluid transfer between a first fluid container and a second fluid container. More specifically, the invention is directed to a connector having structure to increase friction between threaded connection portions and discourage unintended disconnection.

Description of Related Art

Many medical connectors comprise a first component having a female luer-lock element that is arranged to be rigidly joined to a corresponding male luer-lock element of a second connector component that is attached to a medical line or other medical connection, for example. The male-luer lock element can, thus, be freely screwed into and unscrewed from the female luer-lock element. However, once the male luer-lock element has been screwed into the female luer-lock element of the connector, there is a risk that the connector components may be accidentally or inadvertently unscrewed, which could lead to the disconnection of the fluid passage. This may entail a serious contamination risk for a patient and/or any other person in the vicinity of the disconnected medical connector. Such a disconnection risk must especially be avoided when administering toxic fluid, such as cytostatic agents.

In addition, mechanical perturbations, such as vibrations, rubbing, and/or pulling when the connector is in use may act to loosen the connection.

It is, therefore, desirable to provide a connection for enabling fluid transfer between a first fluid container and a second fluid container that provides not only some resistance to disconnection but also an indication to the user when the connection has been made and is sufficiently tight to proceed with the transfer.

SUMMARY OF THE INVENTION

In one embodiment, a medical connector includes a body having a distal end, a proximal end, and a generally cylindrical sidewall extending between the distal end and the proximal end. The connector further includes a helical thread extending radially outward from a surface of the sidewall with the helical thread having a crest portion, flank portions, and a root portion and the flank portions connecting the crest portion to the root portion. At least one deformable protrusion extends radially outward from the root portion of the helical thread.

A first end and a second end of the at least one deformable protrusion may be adjacent the flank portions of the helical thread. A radial height of the at least one deformable protrusion from the surface of the sidewall may be about equal or less than a radial height of the crest portion of the helical thread from the surface of the sidewall. At least one deformable protrusion may be a rib oriented parallel to a central axis of the body of the connector. At least one deformable protrusion may be a rib oriented perpendicular to a central axis of the body of the connector. The at least one deformable protrusion may be detachably connected to at least one flank portion of the helical thread. The at least one deformable protrusion may include a score or a notch as an initiation point for deformation. At least one deformable stop may extend radially outward from the surface of the sidewall at the proximal end of the connector. The circumferential width of the at least one deformable stop may decrease as the radial distance of the deformable stop from the surface of the sidewall increases. The circumferential width of the at least one deformable stop may decrease as the axial distance of the deformable stop from the proximal end of the body increases. The at least one deformable stop may be at a proximal-most end of the helical thread.

The medical connector may further include a mating connector having a body with a distal end, a proximal end, and a generally cylindrical sidewall extending between the distal end and the proximal end, and a helical thread extending radially outward from a surface of the sidewall. The helical thread of the mating connector is adapted to engage the helical thread of the connector. The at least one deformable protrusion may be a triangle-shaped rib. The helical thread may include two offset helical threads. The at least one deformable protrusion may extend between the two helical threads. The medical connector may further include a connector surface positioned adjacent to the proximal end of the body and at least one deformable stop extending from the connector surface. The at least one deformable stop may be configured to engage a distal end of a mating connector when the medical connector is connected with the mating connector.

In another embodiment, a method of connecting two fluid containers includes: providing a connector having a helical thread extending radially outward from a surface of the connector, and a mating connector comprising a helical thread extending radially outward from a surface of the mating connector with the connector including at least one deformable protrusion extending radially outward from a root portion of the helical thread; engaging the helical thread of the mating connector with the helical thread of the connector; advancing the mating connector onto the connector by rotating the mating connector; and engaging the at least one deformable protrusion with the mating connector such that the friction between the connector and the mating connector is increased when the at least one deformable protrusion of the connector is deformed by the helical thread of the mating connector as the mating connector is advanced onto the connector.

The deformation of the at least one deformable protrusion may be in the direction of rotation used to advance the mating connector. The method may further include engaging a stop with the mating connector to stop advancement of the mating connector onto the connector.

In a further embodiment, a medical connector includes a body having a distal end, a proximal end, and a sidewall extending between the distal end and the proximal end, and at least one deformable protrusion extending radially outward from the sidewall of the body with the at least one deformable protrusion configured to engage a helical thread of a mating connector such that friction between the connector and the mating connector is increased when the at least one deformable protrusion of the connector is deformed by the helical thread of the mating connector. The medical connector may further include at least one deformable stop extending radially outward from the surface of the sidewall at the proximal end of the connector.

DESCRIPTION OF THE INVENTION

Figure 1:
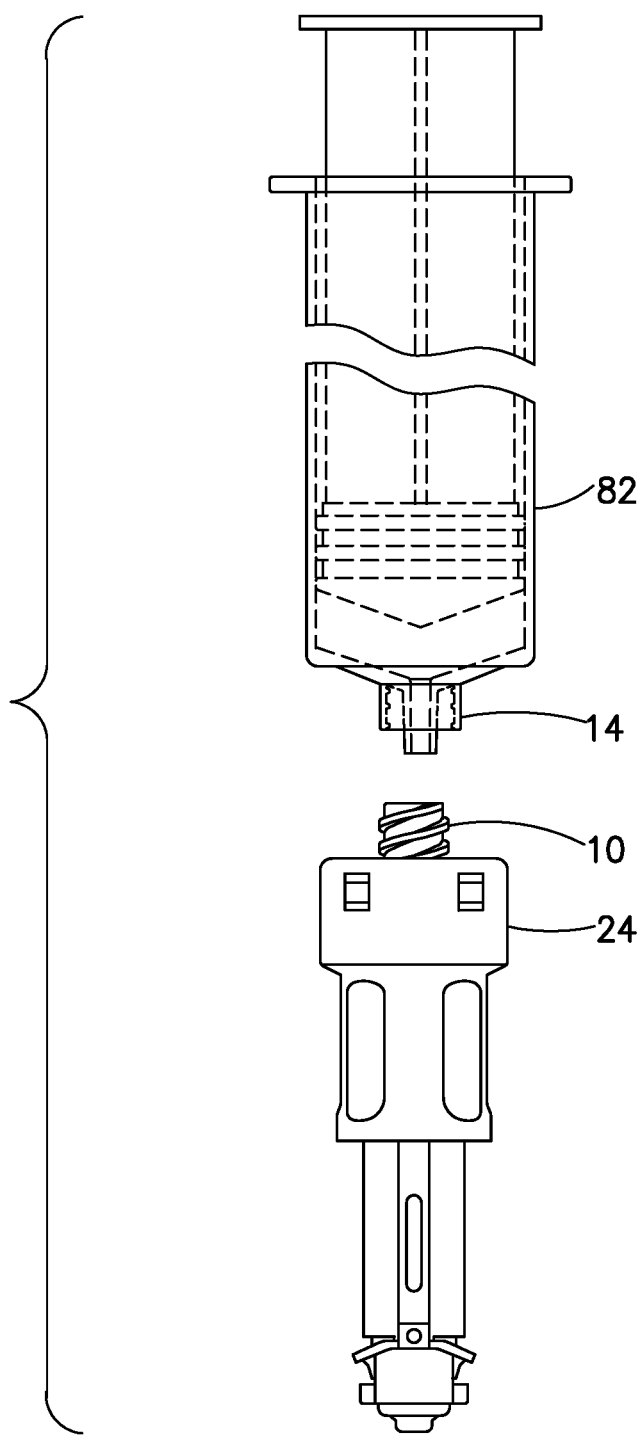
FIG. 1 is a perspective view of a conventional syringe and syringe adapter.

For purposes of the description hereinafter, the terms such as "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

One embodiment of the present invention is directed to a connector 10 for fluidly connecting a first fluid container to a second fluid container to allow the fluid in one of the first or second fluid container to pass into the other of the first or second fluid container. For example, the connector 10 may be utilized in connection with the syringe adapter 24 shown in FIG. 1. A "fluid container" as used herein is intended to mean any vessel that can at least temporarily contain a fluid, including, but not limited to, a vial, a medical line, a tube, or an infusion fluid container, such as an infusion bottle or an infusion bag, a syringe, or a needle protector device.

Referring to FIG. 1, a conventional syringe 82 and syringe adapter 24 are shown. The syringe 82 includes a male luer-lock connector that is configured to be secured to a corresponding female luer-lock connector of the syringe adapter 24. The syringe adapter 24 may be a BD PhaSeal™ Injector commercially available from Becton, Dickinson and Company. The syringe adapter 24 forms part of a closed system transfer device that enables a closed transfer of drugs between containers.

As shown in FIGS. 2A-2C, 4A-7, and 9, the connector 10 includes a body 12 having a distal end 16, a proximal end 18, and a sidewall 20 extending between the distal end 16 and the proximal end 18 and defining a central lumen 22. The sidewall 20 may be generally cylindrical. The connector 10 may be a female luer-lock connector, although other suitable connector arrangements may be utilized. The proximal end 18 of the body 12 of the connector 10 may be attached directly to a first fluid container or may extend from an additional connection portion that connects directly to the fluid container to provide a fluid connection between the first fluid container and the central lumen 22 of the connector 10. The body 12 of the connector 10 may extend from a needle holder of a syringe adapter, such as the syringe adapter 24 shown in FIG. 1. An inner surface of the needle holder may include a projection that cooperates with a body of the syringe adapter 24 to form a ratchet-type connection such that the needle holder is generally free to rotate relative to the body of the syringe adapter 24 in a first direction, but is generally restricted from such relative rotation when rotated in a second, opposite direction.

The body 12 of the connector 10 includes external threads 26 extending radially outward from the external surface 28 of the sidewall 20 and proceeding in a helical fashion from the distal end 16 to the proximal end 18 of the body 12. In the embodiment shown, the body 12 includes two external threads 26, although one or more threads may be provided. The external threads 26 each comprise flank portions 34, 36, a crest portion 38, and a root portion 39. The crest portion 38 and the flank portions 34, 36 together define a helical rib 30 and the root portion 39 and the flank portions 34, 36 together define a helical groove 32. The crest portion 38 of the external threads 26 extends radially a distance from the external surface 28 of the sidewall 20. The helical ribs 30 may have any suitable cross-sectional shape, including but not limited to, square, rounded, and trapezoidal. In the embodiment shown in FIGS. 2A-2C, 4A-7, and 9, the helical rib 30 has a generally trapezoidal cross-section with the crest portion 38 positioned a distance from the external surface 28 of the sidewall 20 and substantially parallel to the external surface 28 of the sidewall 20. The two flank portions 34, 36 extend from the crest portion 38 inward toward the external surface 28 of the sidewall 20. The angle between the flank portions 34, 36 and the root portion 39 is greater than 90° as is the angle between the flank portions 34, 36 and the crest portion 38. The shape of the helical groove 32 is defined by the flank portions 34, 36 and the root portion 39. In the embodiment shown in FIGS. 2A-2C, 4A-7, and 9, the helical groove 32 has a trapezoidal shape. The external threads 26 may extend one or more revolutions around the body 12 of the connector 10 or may be a partial thread that extends less than one revolution around the body 12 of the connector 10.

The connector 10 is configured to be secured to and mate with a mating connector 14, shown in FIGS. 3, 5, 8, and 10 that includes a body 72 having a distal end 74, a proximal end, and a generally cylindrical sidewall 78 extending between the distal end 74 and the proximal end and defining a central lumen 80. The mating connector 14 may be a male luer-lock connector, although other suitable mating connectors may be utilized. The proximal end of the body 72 of the mating connector 14 may be attached directly to a first fluid container, for example, the syringe 82 shown in FIG. 1, or may extend from an additional connection portion that connects directly to the fluid container to provide a fluid connection between the first fluid container and the central lumen 80 of the body 72 of the mating connector 14. In the embodiment shown in FIGS. 3, 5, 8, and 10, the mating connector 14 is a male luer-lock.

Figure 3:
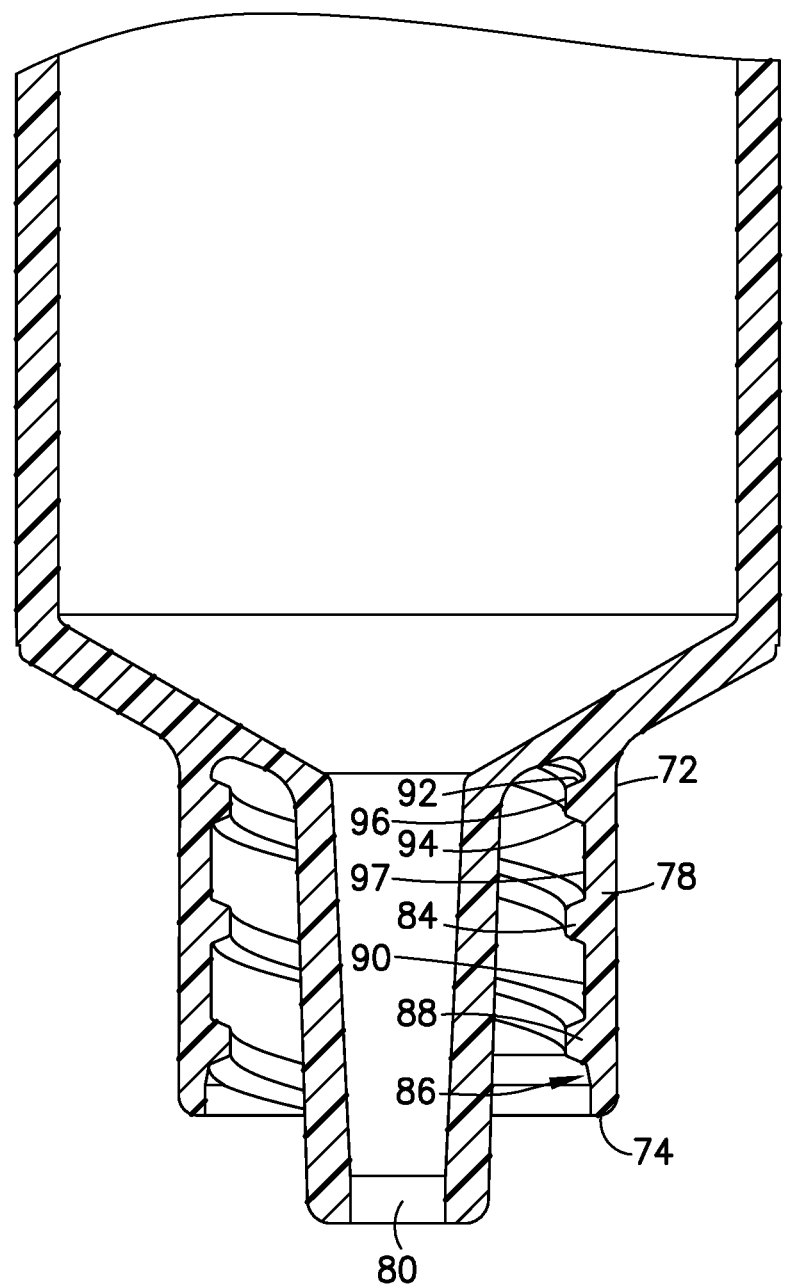
FIG. 3 is a cross-sectional view of a mating connector according to one embodiment of the present application
Figure 5:
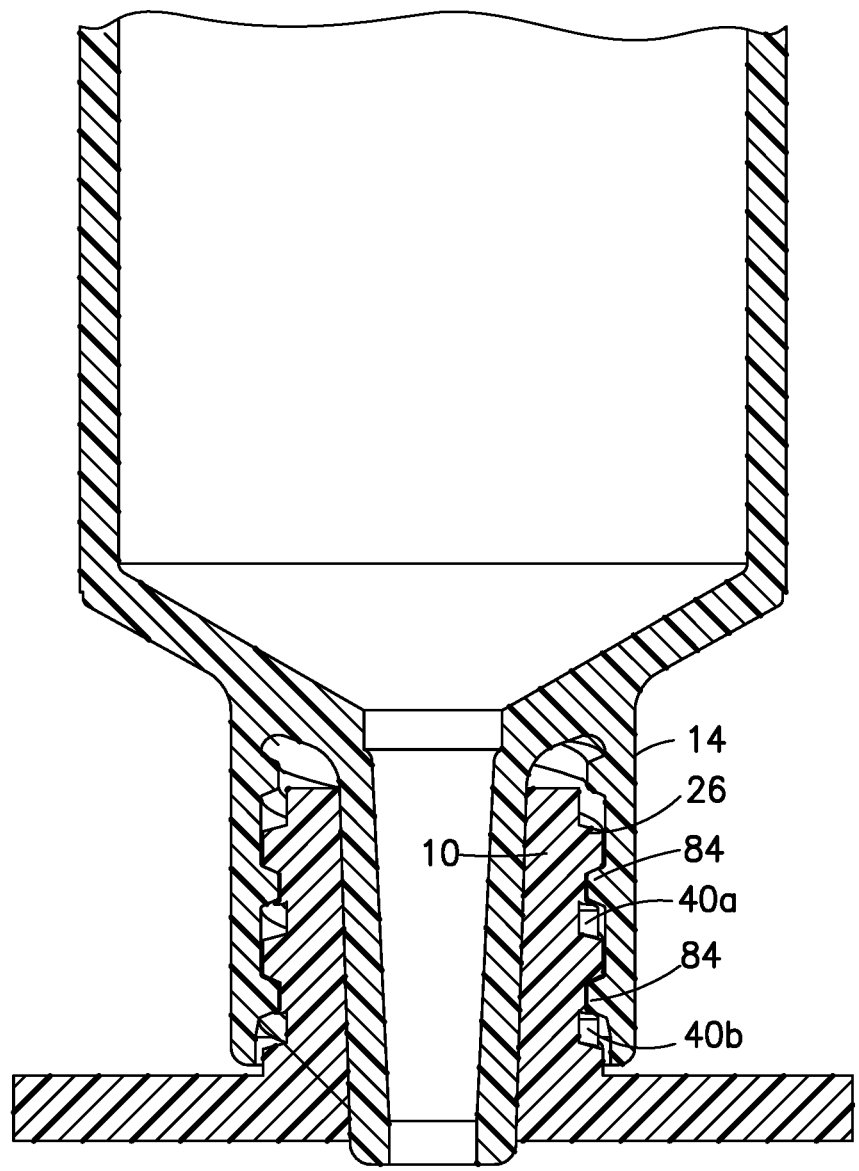
FIG. 5 is a cross-sectional view of the connector shown in FIG. 2A and a mating connector in a connected state according to one embodiment of the present application.

As shown in FIGS. 3 and 5, the body 72 of the mating connector 14 includes internal helical threads 84 extending radially outward from the internal surface 86 of the sidewall 78 and proceeding in a spiral fashion from the distal end 74 to the proximal end of the body 72. In the embodiment shown, the body 72 includes two internal threads 84, although one or more threads may be provided. The internal threads 84 each comprise flank portions 92, 94, a crest portion 96, and a root portion 97. The crest portion 96 and the flank portions 92, 94 together define a helical rib 88 and the root portion 97 and the flank portions 92, 94 together define a helical groove 90. The crest portion 96 of the internal threads 84 extends radially a distance from the internal surface 86 of the sidewall 78. The helical rib 88 may have any suitable cross-sectional shape, including but not limited to, square, rounded, and trapezoidal. The internal threads 84 are shaped and sized to engage the external threads 26 of the connector 10 so that the body 72 of the mating connector 14 can be threaded onto the body 12 of the connector 10 and tightened to form the connection.

In the embodiment shown in FIGS. 3 and 5, the helical ribs 88 have a generally trapezoidal cross-section with the crest portion 96, a distance from the internal surface 86 of the sidewall 78 and substantially parallel to the internal surface 86 of the sidewall 78. The two flank portions 92, 94 extend from the crest portion 96 inward toward the internal surface 86 of the sidewall 78. The angle between the flank portions 92, 94 and the root portion 97 is greater than 90° as is the angle between the flank portions 92, 94 and the crest portion 96. The shape of the helical groove 90 is defined by the flank portions 92, 94 and the root portion 97 of the internal threads 84. In the embodiment shown in FIGS. 3 and 5, the helical groove 90 has a trapezoidal shape.

When a user of the connector 10 desires to make the connection, the mating connector 14 is threaded onto the connector 10, such that the internal threads 84 of the mating connector 14 engage the external threads 26 of the connector 10.

The connector 10 has at least one deformable protrusion 40a, 40b extending radially outward from the root portion 39 of the external thread 26 such that it is generally disposed within the helical groove 32. The deformable protrusion 40a, 40b has a radial height from the external surface 28 of the sidewall 20 that is about equal to or less than the radial height of the crest portion 38 of the external thread 26 from the external surface 28 of the sidewall 20 and a width that may be less than the width of the root portion 39 in the axial direction. The deformable protrusion 40a, 40b may also have a radial height from the external surface 28 of the sidewall 20 that is greater than the radial height of the crest portion 38 of the external thread 26 from the external surface 28 of the sidewall 20. As discussed in more detail below, the deformable protrusions 40a, 40b are configured to deform upon engagement with a helical thread or threads of a mating connector.

Figure 2B:
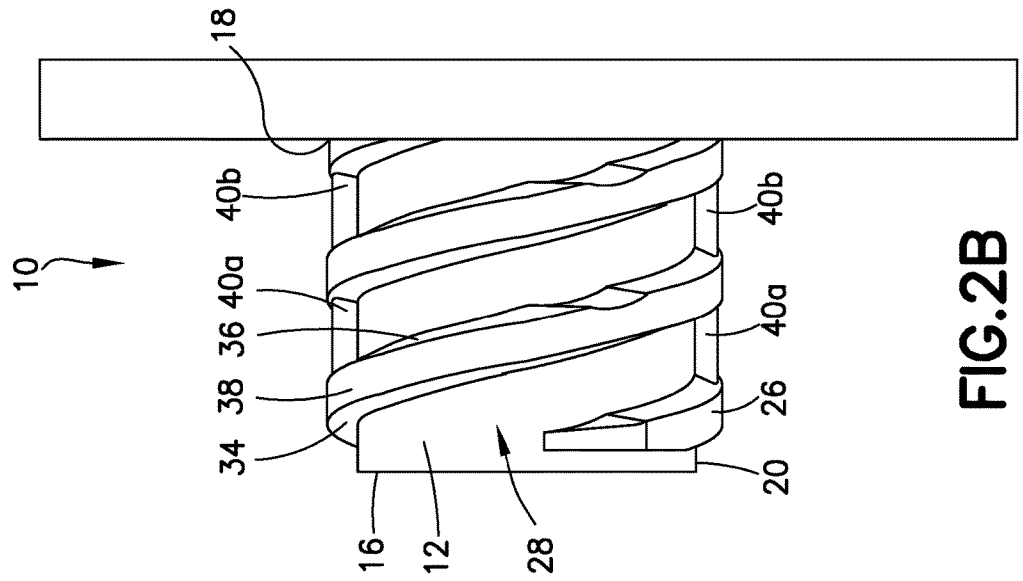
FIG. 2B is a side view of the connector shown in FIG. 2A according to one embodiment of the present application.
Figure 2A:
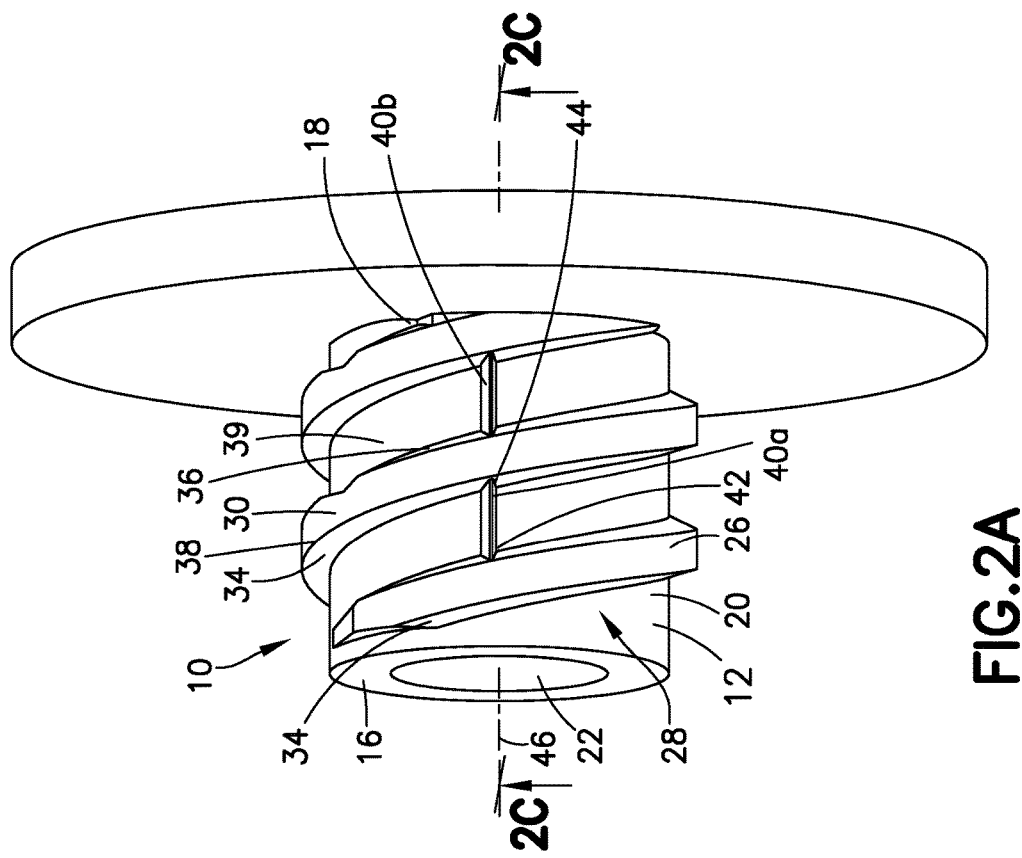
FIG. 2A is a perspective view of a connector according to one embodiment of the present application.
Figure 2C:
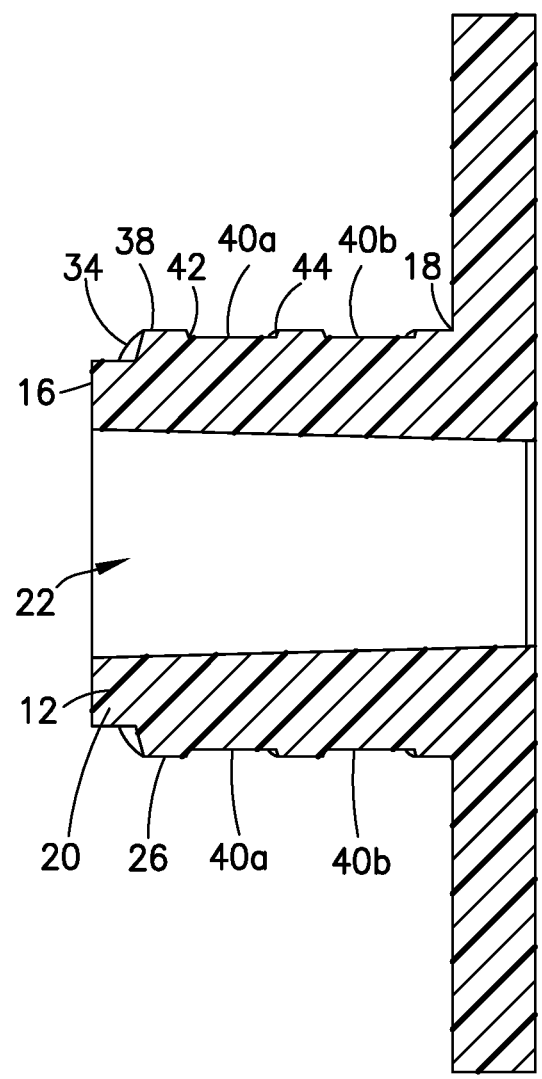
FIG. 2C is a cross-sectional view taken along line 2C-2C shown in FIG. 2A according to one embodiment of the present application.

In the embodiment shown in FIGS. 2A-2C, two deformable protrusions 40a, 40b are disposed in the helical groove 32 such that they form a vertical rib that extends axially along the external surface 28 of the sidewall 20 and is substantially parallel to the central axis 46 the body 12. Each deformable protrusion 40a, 40b extends from a first end 42 adjacent one flank portion 34 of the external thread 26 to a second end 44 adjacent to the other flank portion 36. Further, two sets of deformable protrusions 40a, 40b may be provided to form two vertical ribs, although any other suitable number deformable protrusions may be provided.

Figure 4B:
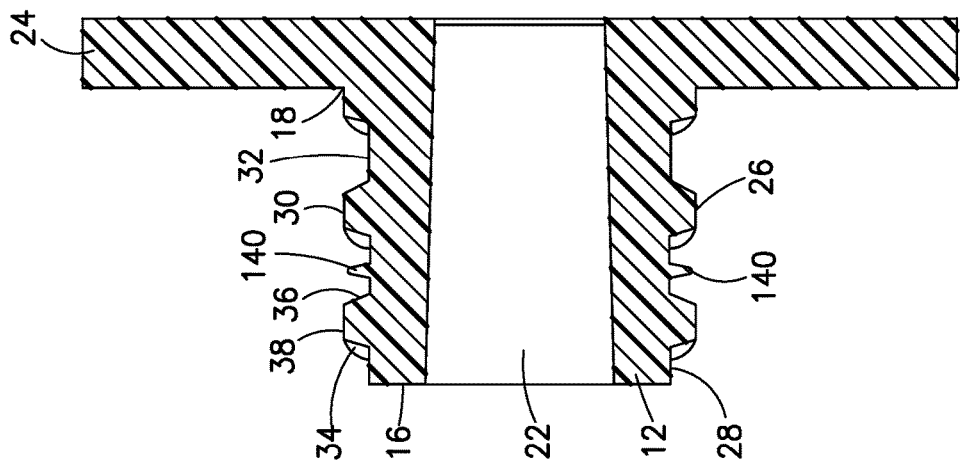
FIG. 4B is a cross-sectional view taken along line 4B-4B shown in FIG. 4A according to one embodiment of the present application.
Figure 4A:
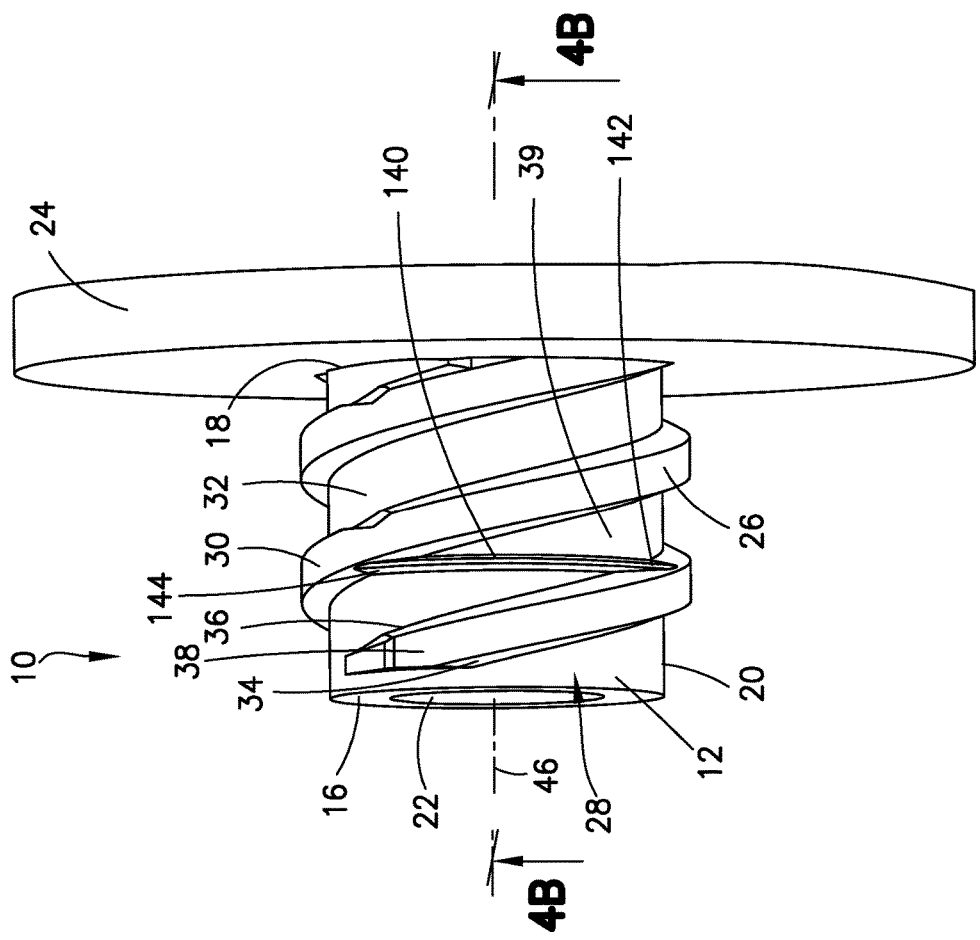
FIG. 4A is a perspective view of a connector according to a second embodiment of the present application.

In the embodiment shown in FIGS. 4A and 4B, a horizontal deformable protrusion 140 is disposed in the helical groove 32 extending circumferentially along the external surface 28 of the sidewall 20 in a direction that is substantially perpendicular to the central axis 46 of the body 12. The deformable protrusion 140 extends from a first end 142 adjacent one flank portion 34 of the external thread 26 to a second end 144 adjacent to the other flank portion 36.

The deformable protrusions 40a, 40b, 140 may or may not be detachably connected to the flank portions 34, 36. The deformable protrusions 40a, 40b, 140 are generally thin, fin-shaped ribs to allow them to deform or bend when a mating connector 14 is threaded onto the connector 10. Any suitable means allowing for deformation of the deformable protrusions 40a, 40b, 140 may be used, including but not limited to, the following arrangements.

The deformable protrusions 40a, 40b, 140 may be constructed to have a geometry such that the geometry combined with the strength of the material used to make the deformable protrusion 40a, 40b, 140 results in the deformable protrusion 40a, 40b, 140 having insufficient strength to withstand the force provided when the deformable protrusion 40, 140 is contacted by the internal threads 84 of a mating connector 14 as the mating connector 14 is threaded onto and advanced onto the connector 10. For example, as shown in FIGS. 2A-2C, 4A, and 4B, the deformable protrusions 40a, 40b, 140 may have the geometry of a very thin, triangular fin-shaped rib, although other suitable shapes for the protrusions may be utilized, such as very thin, rectangular fin-shaped ribs. The resistance to deformation of the deformable protrusions 40a, 40b, 140 is related to its width/thickness in the direction in which force is applied. In the embodiment shown in FIGS. 2A-2C, 4A, and 4B, force will be applied perpendicular to the vertical deformable protrusion 40 and tangential to the horizontal deformable protrusion 140 when the internal thread 84 of the mating connector 14 contacts the deformable protrusion 40a, 40b, 140 during connection of the mating connector 14 and the connector 10. Thus, because, in this direction, the circumferential width of the deformable protrusion 40a, 40b is small, the resistance to deformation will be small allowing the deformable protrusion 40a, 40b to bend in the direction in which the force is applied.

The direction of the vertical deformable protrusions 40a, 40b shown in FIG. 2A and the horizontal deformable protrusion 140 shown in FIG. 4A and their placement extending within the root portion 39 of the external thread 26 from the first flank portion 34 to the second flank portion 36 ensures that the internal thread 84 of the mating connector 14 will always engage the deformable protrusions 40a, 40b, 140 regardless of the dimension of the internal thread 84 or the dimensional tolerance between the connector 10 and the mating connector 14. Therefore, while these deformable protrusions 40a, 40b, 140 are shown as substantially parallel and perpendicular to the central axis 46 of the body 12, respectively, a person skilled in the art will recognize that they may be placed at any angle with respect to the central axis 46 between these two positions as long as they are located such that their direction, and placement in the root portion 39 of the thread 26 and between the flank portions 34, 36 of the thread 26 ensures that the internal thread 84 of the mating connector 14 will always engage the deformable protrusion 40a, 40b, 140 regardless of the dimension of the internal thread 84 or the dimensional tolerance between the connector 10 and the mating connector 14.

Figure 6:
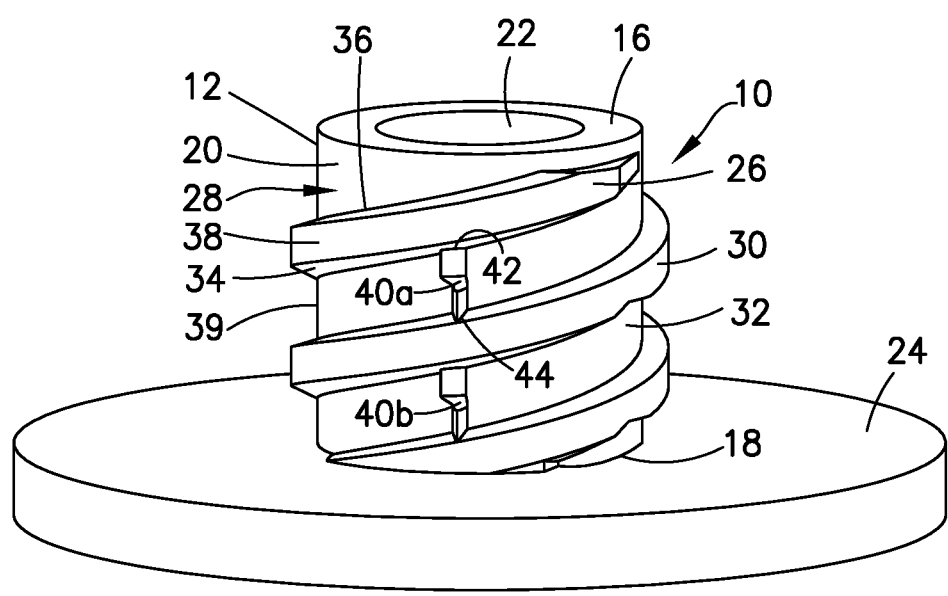
FIG. 6 is a perspective view of the connector shown in FIG. 2A after connection with the mating connector and deformation of the deformable protrusions as shown in FIG. 5.

This can be seen in FIGS. 5 and 6 where a portion, approximately half, of the deformable protrusion 40a, 40b has been bent in the direction of rotation. Since, in this case, the internal thread 84 of the mating connector 14 has an axial width that is less than the axial width of the deformable protrusion 40a, 40b, only a portion of the deformable protrusion 40a, 40b is contacted and deformed by the internal thread 84. The horizontal deformable protrusion 140 shown in FIG. 4A would be similarly deformed.

Although the deformable protrusions 40a, 40b, 140 have high interference with the mating connector 14, the deformable protrusions 40a, 40b, 140 are thin and deformable and, therefore, some of the deformable protrusions 40a, 40b, 140 will be displaced in order to allow the deformable protrusion 40a, 40b, 140 to conform with the internal threads 84 of the mating connector 14. This results in a consistent final contact pressure and, therefore, resistive torque within a relatively large range of connector 10 and mating connector 14 dimensions.

Conventional interference ribs require tight tolerances, as even small interferences create large contact stresses, therefore, the dimensions must be closely controlled if reasonable control of retention forces is to be attained. This can be especially challenging because although connector designs are often specified by regulating bodies, such as ISO, mating connectors made by other manufacturers can vary significantly in dimension even within the standards and may vary from the standards. The deformable protrusions 40a, 40b, 140 of the present invention are less dependent on tight tolerances, as they have high interference and deformation as described above and, because the deformable protrusions 40a, 40b, 140 are being deformed and displaced, the final contact force is far less sensitive to the initial interference.

The deformable protrusions 40a, 40b, 140 according to embodiments of the present invention are also less sensitive to placement and activate more reliably with a wider range of mating connectors 14 than conventional arrangements. Because the internal thread 84 of the connector 10 and the mating connector 14 are both helical, placing a helical crush rib between the primary threads is challenging. There can be a wide range in the permissible width and spacing of the threads 26, 84 of the connector 10 and the mating connector 14, therefore, ensuring the helical crush rib is in the right place for engagement for all possible configurations is difficult. In the present invention, the deformable protrusions 40a, 40b, 140 are not aligned with the external threads 26, and, as described above, engagement is ensured. Alternatively, the deformable protrusion 40a, 40b, 140 could be scored or contain a notch that provides a weak point to act as an initiation point for deformation of the deformable protrusion 40, 140.

The two mechanisms for deformation may also be used in combination. For example, the deformable protrusions 40a, 40b, 140 in the form of a thin, fin-shaped rib may be detachably connected at its first end 42, 142 and second end 44, 144 to the flank portions 34, 36 of the external thread 26 using a scored, thinner, or notched engagement point having less strength than the engagement point between the deformable protrusions 40a, 40b, 140 and the root portion 39 of the external thread 26. In this case, the force provided by the internal threads 84 of a mating connector 14 as the mating connector 14 is threaded onto and advanced onto the connector 10 is sufficient to detach the ends 42, 44, 142, 144 of the deformable protrusions 40a, 40b, 140 from the flank portions 34, 36 of the external thread 26 and further deform the deformable protrusions 40a, 40b, 140 due to its geometry. Alternatively, the deformable protrusions 40a, 40b, 140 may be scored or contain a notch at a point along its radial height to facilitate bending.

The deformable protrusions 40a, 40b may be present in any number, take any shape, size, and cross-section, and be oriented in any direction within the helical groove 32 such that they extend from the root portion 39 into the helical groove 32, act to increase friction when the connector 10 is threaded into a mating connector 14, at least partially contact the internal threads 84 of the mating connector 14, and deform when the connector 10 is threaded into a mating connector 14.

The maximum radial height of any portion of the deformable protrusions 40a, 40b, 140 from the external surface 28 of the sidewall 20 is less than or equal to the maximum height of any portion of the helical rib 30 from the external surface 28 of the sidewall 20.

Any number of deformable protrusions 40a, 40b, 140 may be used and vertical deformable protrusions 40a, 40b may be used in combination with horizontal deformable protrusions 140.

Figure 7:
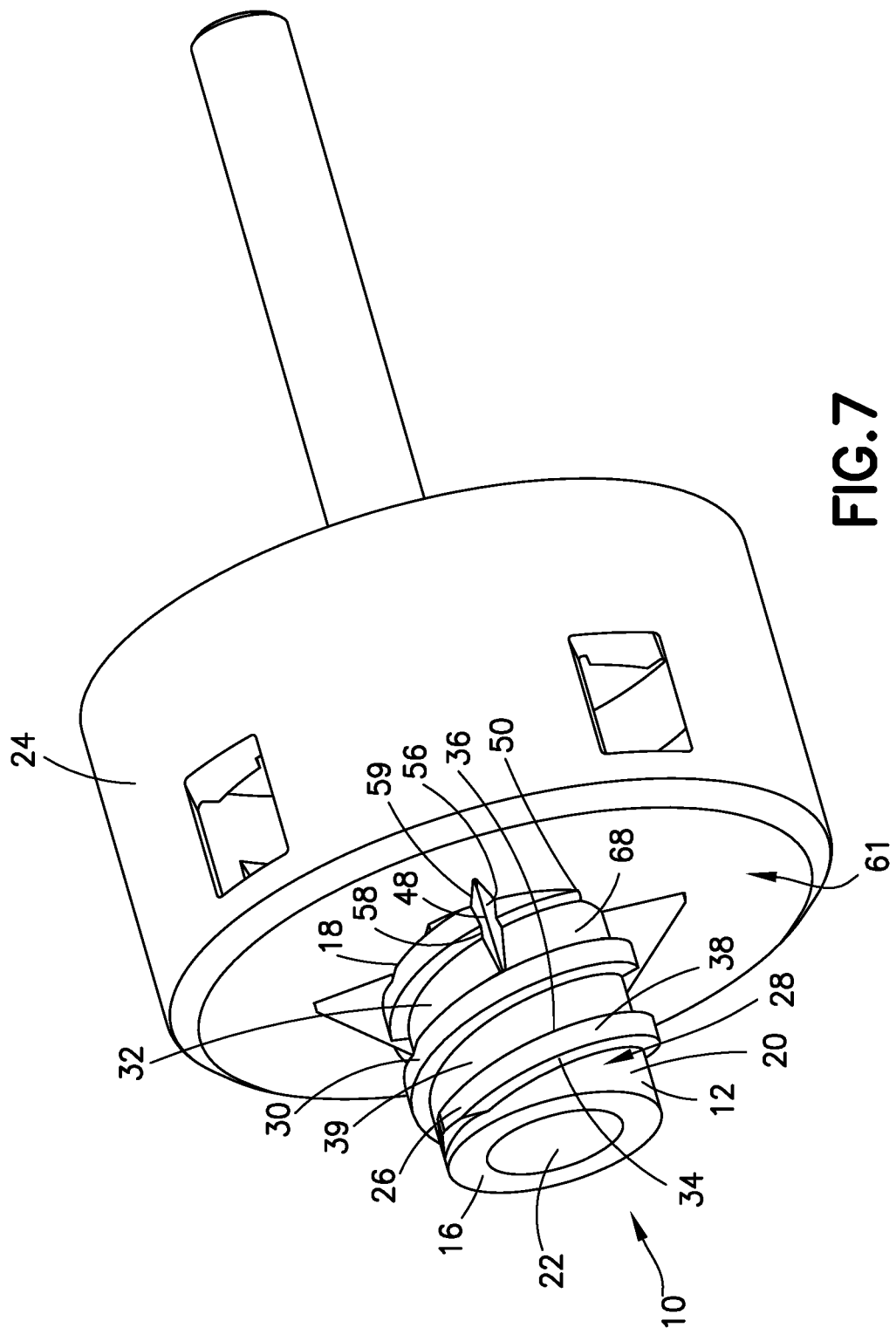
FIG. 7 is a perspective view of a connector according to a third embodiment of the present application.
Figure 8:
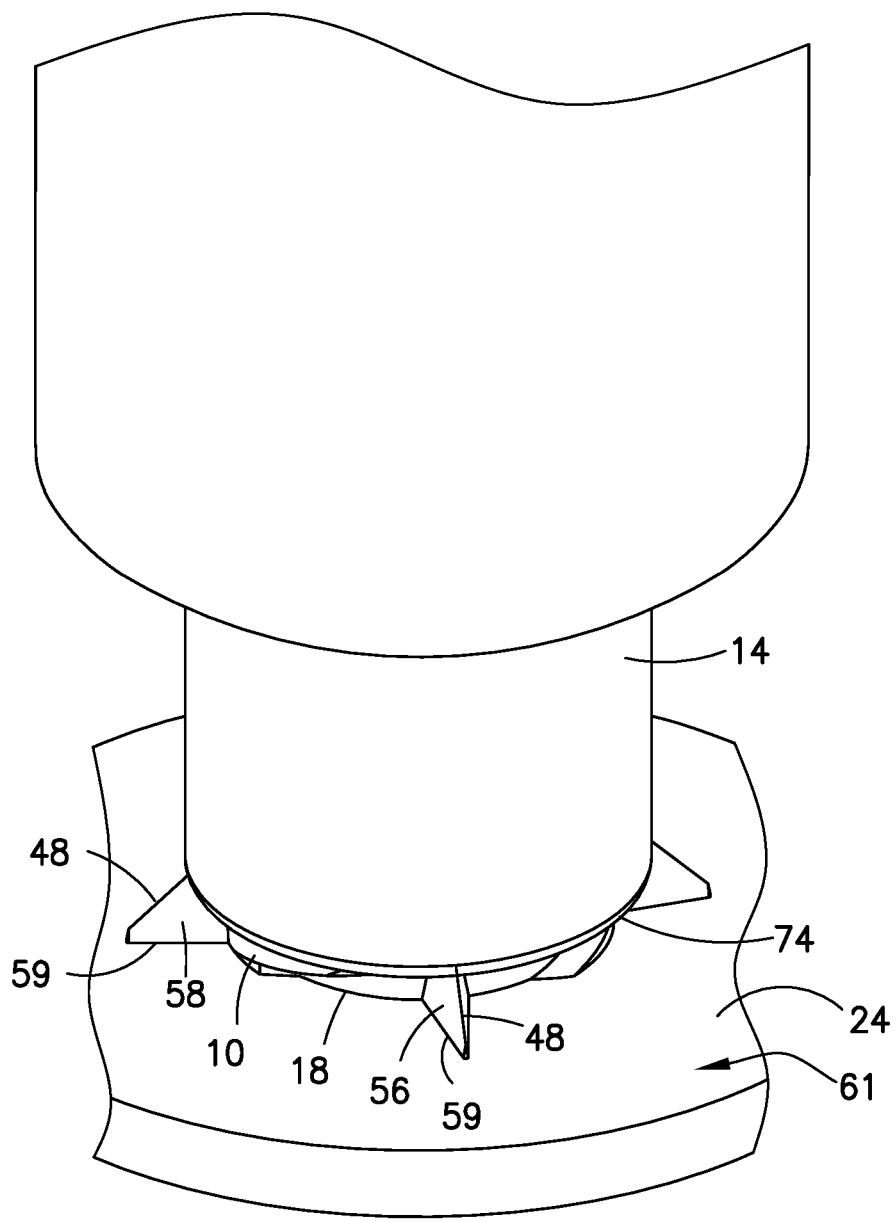
FIG. 8 is a perspective view of the connector shown in FIG. 7 connected with a mating connector according to one embodiment of the present application.

As shown in FIG. 7, at least one deformable stop 48 may be superimposed over a portion of the proximal-most end 50 of at least one of the helical ribs 30. The deformable stop 48 extends from both the root portion 39 of the external thread 26 and the crest portion 38 of the external thread 26. The deformable stop 48 comprises a first side 56, a second side 58, and a bottom 59. The bottom 59 of the deformable stop 48 is connected to the distal surface 61 of a fluid container or a connection portion that will be connected to a fluid container, in this case a syringe adaptor 24. The first side 56 and second side 58 of the deformable stop 48 have a generally triangular surface. As a result, the radial height of the deformable stop 48 from the external surface 28 of the sidewall 20 tapers from the bottom 59 of the deformable stop 48 towards the distal end 16 of the body 12. This results in the radial height of the deformable stop 48 from the external surface 28 of the sidewall 20 being at a maximum at its proximal end 18 adjacent the proximal end 18 of the body 12 and at a minimum at its distal end 16.

The connection of the sides 56, 58 of the deformable stop 48 are at an angle to one another such that, for any plane cutting through the deformable stop 48 perpendicular to the central axis 46 of the body, the deformable stop 48 has a triangular cross-section. More specifically, for any such plane, the radial height of the deformable stop 48 from the external surface 28 of the sidewall 20 is at a maximum at the centerline of the deformable stop 48 and tapers in both directions circumferentially such that the radial height of the deformable stop 48 from the external surface 28 of the sidewall 20 is at a minimum at the circumferentially outermost edges of the sides 56, 58 of the deformable stop 48 which are substantially flush with the external surface 28 of the sidewall 20.

Because the deformable stop 48 has a triangular cross-section perpendicular to the central axis 46 of the body 12, the circumferential width of the deformable stop 48 increases as the distance from the external surface 28 of the sidewall 20 decreases. The resistance to deformation of the deformable stop 48 is directly related to its width/thickness in the direction in which force is applied. In the case of the connector 10, force will be applied perpendicular to the second side 58 of the deformable stop 48 when the internal thread 84 and/or the distal end 74 of the mating connector 14 contacts the deformable stop 48 during connection of the mating connector 14 and the connector 10. Thus, since, in this direction, the circumferential width of the deformable stop 48 increases as the radial distance from the external surface 28 of the sidewall 20 decreases, the resistance to deformation will also increases as the radial distance of the deformable stop 48 from the external surface 28 of the sidewall 20 decreases resulting in the resistive force provided by the deformable stop 48 increasing as the mating connector 14 is advanced onto the connector 10.

Therefore, dependent on the amount of force provided by the internal thread 84 and/or the distal end 74 of the mating connector 14 when the internal thread 84 and/or the distal end 74 contacts the deformable stop 48, a radially outer portion of the deformable stop 48 will deform increasing the friction between the mating connector 14 and the connector 10 while a radially inner portion of the deformable stop 48 will not deform and will act to stop advancement of the mating connector 14. This feature can be seen in FIG. 7 where a radially outer portion of the distal end 74 of the deformable stop 48 has been deformed by the internal threads 84 and/or the distal end 74 of the mating connector 14.

A person skilled in the art can appreciate that the deformable stop 48 can, therefore, be adjusted to provide more friction and less stopping or vice versa by adjusting the geometry of the deformable stop 48 to change the amount by which the circumferential width of the deformable stop 48 increases as the radial distance of the deformable stop 48 from the external surface 28 of the sidewall 20 decreases.

Figure 9:
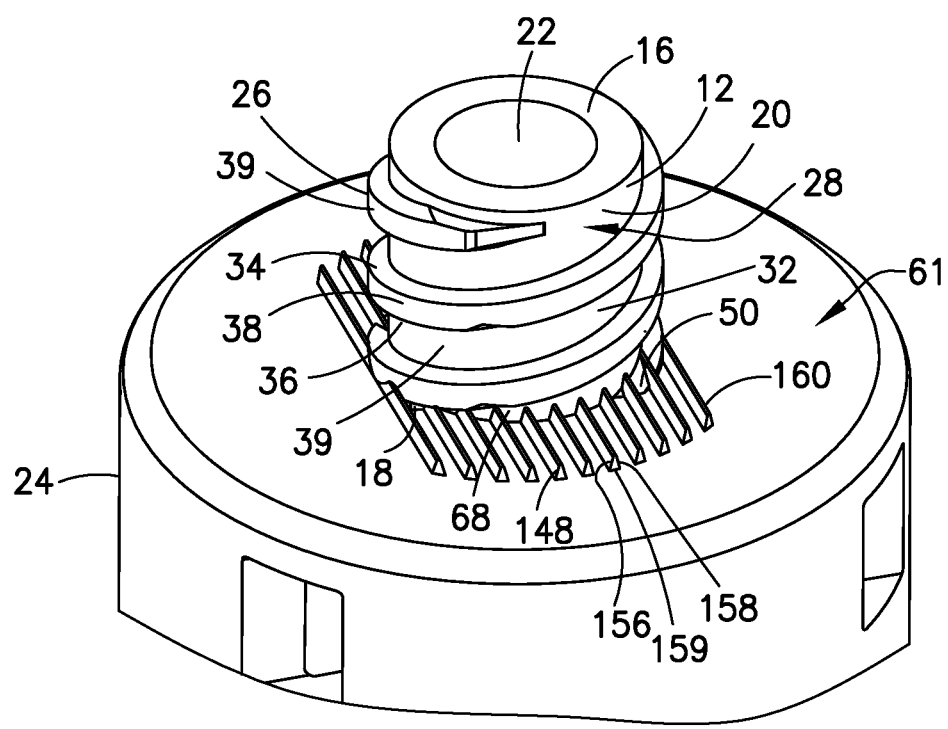
FIG. 9 is a perspective view of a connector according to a fourth embodiment of the present application.

In another embodiment, shown in FIG. 9, a deformable stop 148 may instead comprise a number of portions separated by gaps extending from the proximal-most end 50 of at least one of the helical ribs 30. Each portion of the deformable stop 148 extends radially outward from the external surface 28 of the sidewall 20. Each portion comprises a first side 156, a second side 158, and a bottom 159. The first end 160 of the deformable stop 148 is adjacent the proximal-most end 50 of one of the helical ribs 30 and the deformable stop 148 is generally disposed within the proximal-most end 68 of the helical groove 32.

The connection of the sides 156, 158 of the deformable stop 148 is at an angle to one another such that, the deformable stop 148 has a triangular cross-section in the axial direction. Because the deformable stop 148 has a triangular cross-section in the axial direction, the circumferential width of the deformable stop 148 increases as the axial distance from the proximal end 18 of the body 12 decreases. The resistance to deformation of the deformable stop 148 is related to its width/thickness in the direction in which force is applied. In the case of the connector 10, force will be applied perpendicular to the second side 158 of the deformable stop 148 when the internal thread 84 and/or the distal end 74 of the mating connector 14 contacts the deformable stop 148 during connection of the mating connector 14 and the connector 10. Thus, since, in this direction, the circumferential width of the deformable stop 148 increases as the axial distance from the proximal end 18 of the body 12 decreases, the resistance to deformation will also increase as the axial distance of the deformable stop 148 from the proximal end 18 of the body 12 decreases resulting in the resistive force provided by the deformable stop 148 increasing as the mating connector 14 is advanced onto the connector 10.

Therefore, dependent on the amount of force provided by the internal thread 84 and/or the distal end 74 of the mating connector 14 when the internal thread 84 and/or the distal end 74 contacts the deformable stop 148, an axially distal portion of the deformable stop 148 will deform increasing the friction between the mating connector 14 and the connector 10 while an axially proximal portion of the deformable stop 148 will not deform and will act to stop advancement of the mating connector 14.

Figure 10:
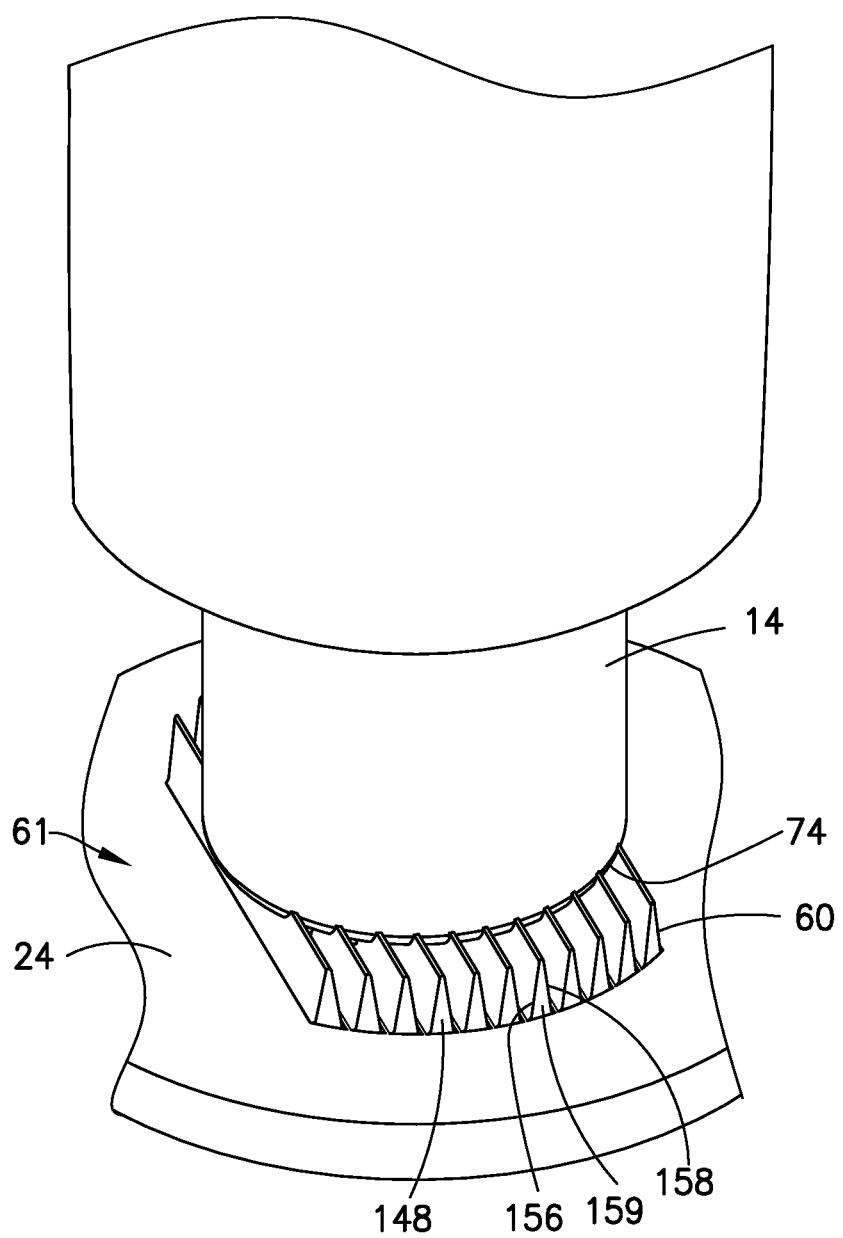
FIG. 10 is a perspective view of connector according to a fifth embodiment of the present application showing the connector connected with a mating connector.

Referring to FIG. 10, a further embodiment of a deformable stop 248 is shown. The deformable stop 248 is similar as the deformable stop 148 shown in FIG. 9, except for the dimensions of the deformable stop 248. In particular, the deformable stop 248 shown in FIG. 10 is taller and thinner than the deformable stop 148 shown in FIG. 9. As shown in FIG. 10, the axially proximal portion of the deformable stop 248 has been deformed by the internal threads 84 and/or the distal end 74 of the mating connector 14.

A person skilled in the art can appreciate that the deformable stops 148, 248 can, therefore, be adjusted to provide more friction and less stopping or vice versa by adjusting the geometry of the stop to change the amount by which the circumferential width of the deformable stops 148, 248 decreases as the axial distance of the deformable stops 148, 248 from the proximal end 18 of the body 12 increases.

When a user of the connector 10 desires to make the connection, the mating connector 14 is threaded onto the connector 10, such that the internal threads 84 of the mating connector 14 engage the external threads 26 of the connector 10. As the user continues to advance the mating connector 14 onto the connector 10, the deformable protrusion 40a, 40b, 140 of the connector 10 is engaged by the internal threads 84 of the mating connector 14 and is at least partially deformed as the internal threads 84 of the mating connector 14 pass over the deformable protrusion 40a, 40b, 140. This results in increased friction and, thus, retention torque between the connector 10 and the mating connector 14. The user must then apply increased torque to continue to advance the mating connector 14 onto the connector 10. This provides an indication to the user that the connection is being made and that the connection is being tightened. The friction may continue to increase as the mating connector 14 is advanced onto the connector 10 when the internal thread 84 of the mating connector 14 engages additional deformable protrusions 40a, 40b, 140 until the distal-most end of the internal thread 84 and/or the distal end 74 of the mating connector 14 contacts the deformable stops 48, 148, 248 at the proximal end 18 of the body 12 of the connector 10. As the user continues to apply torque to the mating connector 14, the distal-most end of the internal thread 84 and/or the distal end 74 of the mating connector 14 of the mating connector 14 deforms at least a radially outer portion of the deformable stop 48 or an axially distal portion of deformable stops 148, 248 such that the internal thread 84 and/or the distal end 74 of the mating connector 14 are engaged in a wedging manner by the deformable stops 48, 148, 248.

As will be appreciated by a person skilled in the art, the number, size, shape, and orientation of the deformable protrusions 40a, 40b, 140 is chosen to provide the desired amount of friction during connection and retention torque after connection and, if desired, may be chosen to increase or decrease any additional friction that is provided as the mating connector 14 is advanced onto the connector 10. The friction provided will increase as the size of the contact area between the deformable protrusion 40a, 40b, 140 and the internal thread 84 of the mating connector 14 increases. This can be accomplished either by increasing the size of the deformable protrusion 40a, 40b, 140 or by increasing the size of the helical rib 88 of the internal thread 84 of the mating connector 14. The friction and retention torque will also increase as the quantity of the deformable protrusions 40a, 40b, 140 is increased. This gives the user a feeling that the connection is constantly getting tighter and helps to avoid over-tightening of the connection.

Deformation of the deformable protrusion 40a, 40b, 140 and deformable stop 48, 148 will be directional. As the mating connector 14 is advanced onto the connector 10, the force that the internal threads 84 and/or the distal end 74 of the mating connector 14 exerts on the deformable protrusions 40a, 40b, 140 and deformable stops 48, 148, 248 will be in the direction of rotation. This will cause the deformable protrusions 40a, 40b, 140 and deformable stops 48, 148, 248 to deform in that direction. If the user tries to disconnect the connectors 10, 14 by reversing the rotation of the mating connector 14, not only will the retention torque provided by the deformed portions of the deformable protrusions 40a, 40b, 140 and the deformable stops 48, 148, 248 act to resist disconnection, but the deformable protrusions 40a, 40b, 140 and deformable stops 48, 148, 248 which are deformed in the direction of the original rotation will act as barbs or stops that will tend to dig into the internal threads 84 and/or the distal end 74 of the mating connector 14 when the direction of rotation is reversed. In addition, if only a portion of the deformable protrusions 40a, 40b, 140 is deformed in the direction of rotation as shown in FIGS. 5 and 6, the remaining un-deformed portion will also act as a barb or stop that will tend to dig into the internal threads 84 of the mating connector 14 when the direction of rotation is reversed. This will increase the torque needed for disconnection resulting in more resistance of the connectors 10, 14 to accidental disconnection.

Thus, the engagement of both the deformable protrusions 40a, 40b, 140 and the deformable stop 48, 148, 248 of the connector 10 with the internal threads 84 and/or the distal end 74 of the mating connector 14 results in increased friction and retention torque as the mating connector 14 is advanced onto the connector 10. This increased friction and corresponding increase in torque to make the connection provide an indication to the user that the connection between the connector 10 and the mating connector 14 is being secured. The increased feeling of tightness that is transferred to the user encourages the user to stop applying torque when the connection is tight and discourages over-tightening of the connection which can result in breakage of the mating connector 14 or the connector 10. In addition, the deformation of the deformable protrusions 40a, 40b, 140 and deformable stops 48, 148, 248 during the connection of the mating connector 14 to the connector 10 provides retention torque which makes the connection more resistant to disconnection than a connection that merely utilizes corresponding internal and external threads and the inherent frictional properties of the material.

While the discussion and figures have described the deformable protrusions 40a, 40b, 140 and the deformable stops 48, 148, 248 in conjunction with the body 12 of the connector 10, it can be appreciated by a person skilled in the art, that the same result may be achieved in the same manner by incorporating the deformable protrusions 40a, 40b, 140 and the deformable stops 48, 148, 248 into the mating connector 14. Further, although the deformable protrusions 40a, 40b, 140 and the deformable stops 48, 148, 248 are shown in conjunction with the connector 10 having external threads 26, such as female luer-lock connector, the deformable protrusions 40a, 40b, 140 and the deformable stops 48, 148, 248 may also be utilized with a connector that does not have the external threads 26. In particular, the deformable protrusions 40a, 40b, 140 and the deformable stops 48, 148, 248 may be provided on a thread-less female luer connector with the threads 84 of the mating connector 14 engaging the deformable protrusions 40a, 40b, 140 and the deformable stops 48, 148, 248 to increase the feeling of tightness and providing retention torque in generally the same manner as described above.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A medical connector comprising:
 a body having a distal end, a proximal end, and a sidewall extending between the distal end and the proximal end;
 a helical thread extending radially outward from a surface of the sidewall and comprising a crest portion, flank portions, and a root portion, the flank portions connecting the crest portion to the root portion; and
 a deformable portion comprising a score or notch as an initiation point for deformation, the deformable portion configured to deform when engaged by a mating connector such that friction and retention torque increases during connection of the medical connector to the mating connector, the deformable portion being configured to provide tactile feedback to a user as the connection between the medical connector and the mating connector becomes progressively tighter.

2. A syringe adapter comprising:
 a medical connector comprising:
  a body having a distal end, a proximal end, and a sidewall extending between the distal end and the proximal end;
  a helical thread extending radially outward from a surface of the sidewall and comprising a crest portion, flank portions, and a root portion, the flank portions connecting the crest portion to the root portion; and
  a deformable portion comprising a score or notch as an initiation point for deformation, the deformable portion configured to deform when engaged by a mating connector such that friction and retention torque increases during connection of the medical connector to the mating connector, the deformable portion being configured to provide tactile feedback to a user as the connection between the medical connector and the mating connector becomes progressively tighter.

3. The medical connector according to claim 1, wherein the deformable portion of the medical connector extends at least partially from the root portion of the helical thread.

4. The medical connector according to claim 3, wherein the deformable portion extends radially outwardly from the surface of the sidewall by a radial height which is equal to or less than a radial height of the crest portion of the helical thread.

5. The medical connector according to claim 1, wherein the score or notch is located between the deformable portion and the root portion of the helical thread, and wherein the at least one deformable portion is detachably connected to at least one flank portion of the helical thread.

6. The medical connector according to claim 1, wherein the deformable portion comprises a rib oriented about parallel to a central axis of the body of the connector.

7. The medical connector according to claim 1, further comprising at least one deformable stop at the proximal end of the body of the connector which acts to stop advancement of the mating connector.

8. The medical connector according to claim 1, further comprising:
the mating connector including a body having a distal end, a proximal end, and a generally cylindrical sidewall extending between the distal end and the proximal end, and a helical thread defining a helical rib extending radially outward from a surface of the sidewall, the helical thread of the mating connector adapted to engage the helical thread of the medical connector,
wherein an axial width of the helical rib of the mating connector is less than a distance between a first end and a second end of the score or notch of the deformable portion of the medical connector.

9. The medical connector according to claim 8, wherein the deformable portion comprises at least one deformable protrusion comprising a first end and a second end adjacent flank portions of the helical thread of the medical connector, and
wherein a distance between the first end and the second end of the at least one deformable protrusion is greater than an axial width of the helical thread of the medical connector and an axial width of the helical rib of the mating connector.

10. The medical connector according to claim 8, wherein the helical rib of the mating connector is configured to deform approximately half of the at least one deformable protrusion when the at least one deformable protrusion is deformed by the helical rib of the mating connector.

11. The syringe adapter according to claim 2, wherein the deformable portion of the connector extends at least partially from the root portion of the helical thread.

12. The syringe adapter according to claim 11, wherein the deformable portion extends radially outwardly from the surface of the sidewall by a radial height which is equal to or less than a radial height of the crest portion of the helical thread.

13. The syringe adapter according to claim 2, wherein the score or notch is located between the deformable portion and the root portion of the helical thread, and wherein the at least one deformable portion is detachably connected to at least one flank portion of the helical thread.

14. The syringe adapter according to claim 2, wherein the deformable portion comprises a rib oriented about parallel to a central axis of the body of the connector.

15. The syringe adapter according to claim 2, further comprising at least one deformable stop at the proximal end of the body of the connector which acts to stop advancement of the mating connector.

16. The syringe adapter according to claim 2, further comprising:
the mating connector including a body having a distal end, a proximal end, and a generally cylindrical sidewall extending between the distal end and the proximal end, and a helical thread defining a helical rib extending radially outward from a surface of the sidewall, the helical thread of the mating connector adapted to engage the helical thread of the medical connector,
wherein an axial width of the helical rib of the mating connector is less than a distance between a first end and a second end of the score or notch of the deformable portion of the medical connector.

17. The syringe adapter according to claim 16, wherein the deformable portion comprises at least one deformable protrusion comprising a first end and a second end adjacent flank portions of the helical thread of the medical connector, and
wherein a distance between the first end and the second end of the at least one deformable protrusion is greater than an axial width of the helical thread of the medical connector and an axial width of the helical rib of the mating connector.

18. The syringe adapter according to claim 16, wherein the helical rib of the mating connector is configured to deform approximately half of the at least one deformable protrusion when the at least one deformable protrusion is deformed by the helical rib of the mating connector.

\* \* \* \* \*

UNITED STATES PATENT AND TRADEMARK OFFICE
CERTIFICATE OF CORRECTION

PATENT NO. : 10,518,077 B2
APPLICATION NO. : 15/837399
DATED : December 31, 2019
INVENTOR(S) : Andrew Wong It is certified that error appears in the above-identified patent and that said Letters Patent is hereby corrected as shown below:

In the Claims

Column 12, Line 64, Claim 4, delete "outerwardly" and insert -- outwardly --

Column 13, Line 45, Claim 12, delete "outerwardly" and insert -- outwardly --

Signed and Sealed this
Seventeenth Day of March, 2020

Andrei Iancu
*Director of the United States Patent and Trademark Office*